United States Patent [19]

Pompei

[11] Patent Number: 4,763,522
[45] Date of Patent: Aug. 16, 1988

[54] RADIATION DETECTOR PSYCHROMETER

[75] Inventor: Francesco Pompei, Wayland, Mass.

[73] Assignee: Exergen Corporation, Natick, Mass.

[21] Appl. No.: 926,356

[22] Filed: Oct. 31, 1986

[51] Int. Cl.$^4$ ............................................. G01N 25/62
[52] U.S. Cl. ....................................... 73/338; 374/121
[58] Field of Search .................... 73/338, 338.3, 338.6, 73/335, 336, 77; 374/109, 121

[56] References Cited

U.S. PATENT DOCUMENTS

| | | | |
|---|---|---|---|
| 1,933,283 | 10/1933 | Schwartz | 73/338 X |
| 1,938,074 | 12/1933 | Lanquetin | 73/338 |
| 2,589,557 | 3/1952 | Lamb | 73/338 |
| 3,048,038 | 8/1962 | Johnson | 73/338 |
| 3,645,134 | 2/1972 | Kreiberg | 73/338 |

FOREIGN PATENT DOCUMENTS 1203555  1/1960  France .................................. 73/335

OTHER PUBLICATIONS

T. Baumeister (Ed.), "Mark's Standard Handbook for Mechanical Engineers", Eighth Edition, pp. 4–31.

Primary Examiner—John Chapman
Assistant Examiner—Joseph W. Roskos
Attorney, Agent, or Firm—Hamilton, Brook, Smith & Reynolds

[57] ABSTRACT

A hand held testing surface and scale card may be used in conjunction with a radiation detector to obtain an indication of relative humidity. The scale card is provided with two sections. One section is of absorbent relatively thin material; the second section is of non-absorbent material. The absorbent section is wetted by the user just prior to detection and cooled by evaporation. A radiation detector is then able to sense a wet bulb temperature from the wetted and cooled absorbent section. The section of non-absorbent material is kept dry. From this dry section, the radiation detector senses a dry bulb temperature. Using the sensed wet bulb and dry bulb temperatures, the user calculates the relative humidity and dew point temperature form the scales provided on the card.

21 Claims, 2 Drawing Sheets

RADIATION DETECTOR PSYCHROMETER

BACKGROUND

Many methods are available for measuring humidity. An old and most commonly used method is the "sling psychrometer". This method uses two mercury thermometers, one of which has a wet sock on its bulb. The two thermometers are slung rapidly through the air so that the water in the wet sock evaporates, thus cooling the wet bulb to what's known as the wet bulb temperature, and so that the dry bulb is brought to normal air temperature. The wet bulb and dry bulb temperatures are then used to determine the humidity through well known calculations or simplified tables. A disadvantage of the "sling" method lies in the possibility that someone or something could get hit by the slinging psychrometer. A second disadvantage is the slinging time it takes for the water in the wet sock to evaporate and cool the wet bulb to a true wet bulb temperature. Often the user has to sling the psychrometer for such a long time that he does not have the time or energy to repeat the method for a double check.

A further disadvantage of the "sling psychrometer" is the limited accuracy of the method. The wet bulb temperature is measured on the inside of the wet sock instead of on the air-water interface side of the wet sock where there is a true wet-bulb temperature. The wet bulb of the sling psychrometer is actually cooled by a temperature gradient across the sock and consequently does not always achieve the true wet-bulb temperature.

DISCLOSURE OF THE INVENTION

Radiation detectors have been used to provide accurate temperature readings in various applications. Few if any radiation detectors however, have been used in the field of psychrometer. Yet radiation detectors are ideal for overcoming the disadvantages of sling psychrometers because they are accurate, fast and safe.

A wet bulb and dry bulb temperature reading can be obtained with a radiation sensing device from surfaces which hold wet and dry bulb temperatures. A wet surface must be thick enough to hold water yet thin enough to cool quickly upon a passing of air across it. The evaporation cooling principle applies to the wet surface to achieve a wet bulb temperature. The radiation detector senses the cooled air-water interface of the surface before the surface reheats to air temperature to provide a wet bulb temperature reading. A dry surface which is preferably of a thin non-absorbent material is brought to equilibrium with the air temperature. The radiation detector senses a dry bulb temperature from that surface. Thus with such surfaces a radiation detector can be used as a psychrometer which is fast, accurate and safe to use.

In the preferred embodiment of the present invention a radiation detector obtains wet bulb and dry bulb temperatures from a hand held testing card. The testing card has two test surfaces. One section of the testing surface is wetted with a drop of a water based liquid. The other surface is kept dry. Air is passed across the two surfaces by the user waving the testing card once or twice in the air. This waving causes the water in the wet section of the testing surface to evaporate. The evaporation of the water from the wet section causes the wet section to cool. Waving the testing surface twice in the air by the user extending his arm at the elbow in a jerking manner is enough to cool the wet section to the wet bulb temperature. During this same time, the dry section is brought to the temperature of the air. The card thus provides surfaces from which the wet bulb and dry bulb temperatures may be sensed by the radiation detector. The radiation detector is fast enough to sense the temperatures of interest from the testing surface before the wet section reheats to air temperature.

Further, in order to obtain absorption of the infared energy to be detected, the water film of the wet section must be sufficiently opague to the heat energy and thus at least $5 \times 10^{-3}$ cm thick. Thus, the wet testing surface is made of thin, porous yet absorbent material which is thick enough to hold the necessary amount of water for evaporation cooling yet thin enough to allow for quick cooling upon being waved in the air. Also, the testing surface material has a mass sufficient to hold the evaporated water temperature long enough for an accurate measurement of the cooled temperature to be obtained. A paper towel or filter material are suitable materials for the wet testing surface. A piece of paper towel about 0.1 mm thick is thick enough to hold a sufficient cooled water film for a sufficient amount of time. The 0.1 mm thick paper towel is also thin enough to allow cooling by evaporation in a relatively short amount of time.

The dry testing surface is made of a non-absorbent material which is thin enough to be responsive to the temperature of the air. Waxed paper or opague plastic are suitable materials.

The paper towel and waxed paper surfaces are held by a simple frame which is divided into two sections. The two sections of paper towel are totally separated so as to provide and hold the separate surfaces for the wet bulb temperature and dry bulb temperature. Further, the frame does not have a backing placed behind the two sections so that the held material is the sole surface which is detected. A backing would conduct heat to the water film of the wet section of paper towel. Such heat conduction would cause an inaccurate temperature to be sensed by the radiation detector. Thus, the frame freely holds the two separate sections of the materials from which the temperatures of interest are sensed.

BRIEF DESCRIPTION OF THE DRAWINGS

The foregoing and other objects, features and advantages of the invention will be apparent from the following more particular description of the preferred embodiments of the invention, as illustrated in the accompanying drawings in which like reference characters refer to the same parts throughout the different views. The drawings are not necessarily to scale, emphasis instead being placed upon illustrating the principles of the invention.

DESCRIPTION OF PREFERRED EMBODIMENT

Figure 2:
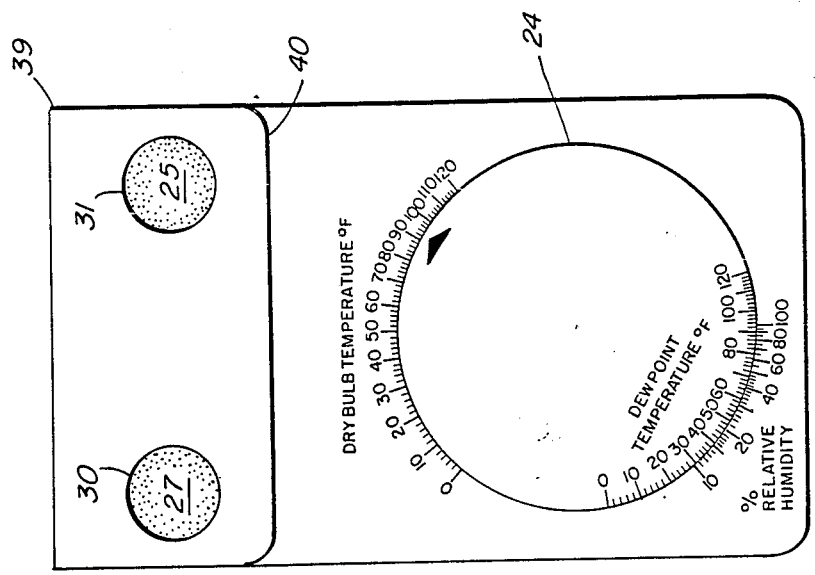
FIG. 2 is a rear view of the embodiment of FIG. 1.

A psychrometer surface testing and scale card 12 comprises a rectangular plastic backing 14. The backing 14 has approximate dimensions of about 4¾ inches by about 3 inches by about 1/16 inch. A relative humidity-scale 16 is positioned at one end of the plastic backing 14. Such scales are available, for example, from American Slide Chart Corp. and are used with conventional psychrometers. One determines relative humidity from wet and dry bulb temperatures by rotating a scaled disc.

Two circular holes 20 and 22 are positioned at the outer end of plastic backing 14. Across hole 22 is a section of paper towel 25 and across hole 20 is a section of waxed paper 27. The two pieces of material 25 and 27 are held in place around their circumferences by plastic backing 14 in a frame-like fashion. Paper towel section 25 and waxed paper section 27 are thus suspended by plastic backing 14 and have no support within their respective circumferences from behind by plastic backing 14 as shown in FIG. 2.

Further, the backside of card 12 at the outer end holding holes 20 and 22 comprises flap 40 as shown in FIG. 2. Flap 40 is formed from a continuation of the front of card 12 which is folded at the outer end at edge 39. Flap 40 comprises holes 30 and 31 which are continuations of holes 20 and 22 respectively from the front side of card 12. Hence, flap 40 provides the back of the frame support of testing sections 25 and 27. Also, flap 40 is sufficiently stiff and folded close enough to the back side of card 12 to hold paper towel section 25 and waxed paper section 27 in place. Because flap 40 is closed only on one side at edge 39, it enables easy replacement of testing sections 25 and 27.

Waxed paper piece 27 is kept dry. Upon the passing of air across waxed paper piece 27, the piece 27 is brought to air temperature which can be detected by a radiation sensor. By detecting the air temperature from the waxed paper piece 27, the user is provided with a dry bulb temperature of interest.

Paper towel piece 25 is able to hold a drop of water or water based liquid which produces a water film thick enough to be substantially opaque to the heat energy of interest. Paper towel piece 25 is thick enough to hold the evaporated water temperature long enough to be detected. Paper towel piece 25 is also thin enough to act as a low conductance path across its span. In turn, piece 25 is conducive to quick evaporation cooling across its thickness upon the passing of air across it. Once paper towel piece 25 is cooled by evaporation of the drop of water-based liquid, a radiation detector can sense the wet bulb temperature from the water film generated by paper towel piece 25.

With the sensed dry and wet bulb temperatures, the user can obtain a relative humidity reading from the scale 16. Then, from the relative humidity and the sensed dry bulb temperature, the user can obtain a dew point temperature reading from a dew point scale 24 positioned on the backside of card 12.

Card 12 comprises a thin, flexible material such as plastic or cardboard which enables easy handling during use of the card. It is preferred that card 12 can be thin and flexible enough to slightly bend when waved in the air by a short light jerking motion, yet stiff enough to flex back after slightly bending in the one direction. Hence, card 12 experiences a flopping backing and forth motion when waved in the air to achieve wet and dry bulb temperatures. The flopping motion quickens the process of passing air across the testing surfaces 25 and 27. As a result, the wet and dry bulb temperatures of interest are quickly and easily achieved. This also allows the user to have more time and energy for a second testing unlike "sling" psychrometers of prior art.

Figure 1:
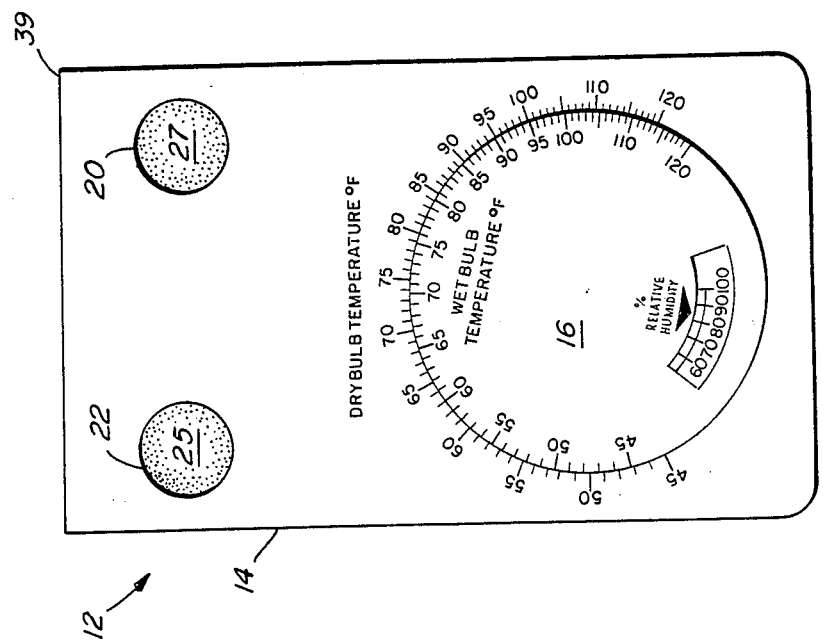
FIG. 1 is a front view of a preferred embodiment of the invention.
Figure 3:
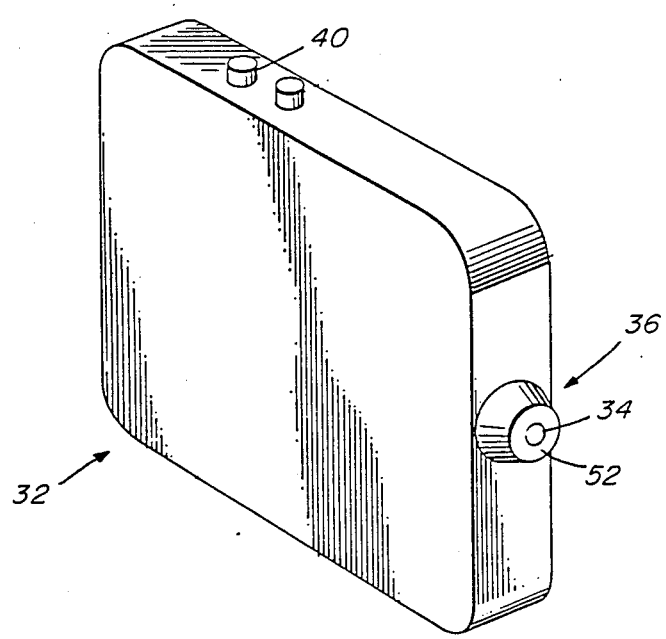
FIG. 3 is a perspective view of a radiation detector for use with the present invention.

The card 12 of FIGS. 1 and 2 has been developed for use with the radiation detector 32 shown in FIG. 3. That detector is shown in greater detail in U.S. patent application Ser. No. 750,524 filed by Francesco Pompei and Shiraz Daya and assigned to the assignee of the present application. The detector 32 is operated by switch 40. The detector has a cup 36 having a low emissivity inner surface 52. Radiation is detected through an aperture 34 in the cup. The cup allows for accurate detection of temperature without regard for the emissivity of the detected surface. The holes 20 and 22 in card 12 need to be greater than the field of view of the detector. Hence, holes 20 and 22 are sufficiently large to enable the cup 36 to be placed within them so that only the test surfaces are viewed. On the other hand, to minimize the amount of water-based liquid required to wet the wet surface, the diameter of the holes should not be much greater than that of the cup. A hole diameter of about $\frac{3}{8}$ inch and a cup diameter of about $\frac{1}{4}$ inch are preferred.

While the invention has been particularly shown and described with reference to a preferred embodiment thereof, it will be understood by those skilled in the art that various changes in form and details may be made therein without departing from the spirit and scope of the invention as defined by the appended claims.

I claim:

1. A psychrometer comprising:
   water film means in which a water film provides sufficient opaqueness such that a wet bulb temperature can be obtained from the water film after said water film reaches equilibrium temperature to be measured;
   a radiation detector for providing an indication of the wet bulb temperature from the water film means after the water film reaches equilibrium temperature; and
   dry means from which the radiation detector senses a dry bulb temperature and provides an indication of the dry bulb temperature.

2. A psychrometer as claimed in claim 1 wherein said water film means includes an amount of water held in a flat sheet of absorbent material which has a thickness large enough to hold a wet bulb temperature for a sufficient amount of time to obtain a measurement of the wet bulb temperature, and small enough such that equilibrium temperature is quickly and easily achieved by passing air across said flat sheet.

3. A psychrometer as claimed in claim 2 wherein said flat sheet is held in a frame-like structure without a backing behind said flat sheet.

4. A psychrometer as claimed in claim 1 wherein said dry means from which the radiation detector senses and provides the dry bulb temperature includes a dry sheet of nonabsorbent material.

5. A psychrometer as claimed in claim 1 wherein said water film means and dry means are mounted to a card, the card having means thereon for determining relative humidity from the wet and dry temperatures.

6. A psychrometer as claimed in claim 1 wherein the radiation detector comprises a cup having a low emissivity inner surface and having an aperture therein through which radiation is detected, such that temperature of a surface can be detected by placing the cup against the surface.

7. A psychrometer as claimed in claim 6 wherein the water film means is a flat sheet of absorbent material stretched across an opening in a card.

8. A psychrometer as claimed in claim 7 further comprising means on the card for determining relative humidity from wet and dry bulb temperatures.

9. A psychrometer comprising a card having:

a flat sheet of absorbent material stretched across an opening in the card, said flat sheet when wetted and cooled by evaporation providing a wet bulb temperature;

means for providing a dry bulb temperature; and means thereon for determining relative humidity from dry and wet bulb temperatures.

10. A psychrometer as claimed in claim 9 wherein the means for providing a dry bulb temperature includes a flat sheet of non-absorbent material stretched across a second opening in the card to provide a dry bulb temperature.

11. A psychrometer as claimed in claim 10 wherein the openings are formed in the card such that easy replacement of said flat sheets of absorbent and non-absorbent material is enabled.

12. A psychrometer as claimed in claim 10 wherein said openings are formed in one end of the card and continue through a flap of the card which is formed by a continuation of the one end of the card that is folded over to one side of the card, the flap enabling easy replacement of said flat sheets of absorbent and non-absorbent material.

13. A psychrometer as claimed in claim 9 wherein said card comprises a flexible plastic which enables the card to slightly flex from side to side when waved in the air by a slight jerking motion, said flexing side to side in the air enhancing the cooling by evaporation of the wetted flat sheet and thereby quickly and easily providing a wet bulb temperature.

14. A psychrometer comprising:

a radiation detector; and a card, the card having a flat sheet of absorbent material stretched across an opening therein to provide a wet bulb temperature, a flat sheet of non-absorbent material stretched across a second opening therein to provide a dry bulb temperature, and means thereon for determining relative humidity from wet and dry bulb temperatures sensed by the radiation detector from said flat sheets of absorbent and non-absorbent material, respectively.

15. A psychrometer as claimed in claim 14 wherein the radiation detector comprises a cup having a low emissivity inner surface and having an aperture therein through which radiation is detected such that temperature of a surface can be detected by placing the cup against the surface.

16. A method of measuring humidity comprising the steps of:

wetting a flat sheet of absorbent material and passing air across the wetted flat sheet such that a wet bulb temperature is achieved;

measuring the wet bulb temperature from the wetted and aired flat sheet using a radiation detector;

measuring a dry bulb temperature from a separate dry surface using the radiation detector; and determining humidity from the measured wet and dry bulb temperatures.

17. A method as claimed in claim 16 wherein the radiation detector comprises a cup having a low emissivity inner surface and having an aperture therein through which radiation is detected, such that temperature of the wetted and aired flat sheet and of the dry surface can be separately detected by respectively placing the cup against said wetted and aired sheet and then against said dry surface.

18. A method as claimed in claim 17 wherein the absorbent flat sheet is stretched across one opening in a card, and the dry surface is a piece of non-absorbent material stretched across a second opening in the same card, said card further comprising means thereon for determining relative humidity from the measured wet and dry bulb temperatures.

19. A method as claimed in claim 18 wherein said card comprises a flexible material such that the step involving passing air across the wetted flat sheet includes waving the card in the air by a slight jerking motion such that the card flexes from side to side causing the wetted flat sheet to be cooled by evaporation and thereby achieve wet bulb temperature.

20. A psychrometer comprising a card having:

a flat sheet of absorbent material stretched across an opening in the card, said flat sheet when wetted and cooled by evaporation providing a wet bulb temperature;

a flat sheet of non-absorbent material stretched across a second opening in the card to provide a dry bulb temperature; and the card further comprising means thereon for determining relative humidity from dry and wet bulb temperatures.

21. A psychrometer as claimed in claim 20 wherein the openings are formed in the card such that easy replacement of said flat sheets of absorbent and non-absorbent material is enabled.

* * * * *